United States Patent
Carucci et al.

(10) Patent No.: US 11,090,271 B2
(45) Date of Patent: Aug. 17, 2021

(54) SOFT GELATIN CAPSULES CONTAINING HYDROXYPROPYL BETA CYCLODEXTRIN WITH HIGH STABILITY

(71) Applicant: ALTERGON S.A., Lugano (CH)

(72) Inventors: Simone Carucci, Lugano (CH);
Maurizio Marchiorri, Lugano (CH);
Marco Pontiggia, Lugano (CH);
Tiziano Fossati, Lugano (CH)

(73) Assignee: ALTERGON S.A., Lugano (CH)

( * ) Notice: Subject to any disclaimer, the term of this patent is extended or adjusted under 35 U.S.C. 154(b) by 0 days.

(21) Appl. No.: 16/479,262

(22) PCT Filed: Feb. 9, 2018

(86) PCT No.: PCT/EP2018/053244
§ 371 (c)(1),
(2) Date: Jul. 19, 2019

(87) PCT Pub. No.: WO2018/146237
PCT Pub. Date: Aug. 16, 2018

(65) Prior Publication Data
US 2019/0374475 A1    Dec. 12, 2019

(30) Foreign Application Priority Data
Feb. 10, 2017    (IT) .................. 102017000015145

(51) Int. Cl.
*A61K 9/48*     (2006.01)
*A61K 47/69*    (2017.01)
*A61K 31/196*   (2006.01)
*A61K 31/4985*  (2006.01)

(52) U.S. Cl.
CPC .......... *A61K 9/4825* (2013.01); *A61K 9/4816* (2013.01); *A61K 31/196* (2013.01); *A61K 31/4985* (2013.01); *A61K 47/6951* (2017.08)

(58) Field of Classification Search
CPC ........................... A61K 31/196; A61K 9/4825
See application file for complete search history.

(56) References Cited

U.S. PATENT DOCUMENTS 8,728,519 B2    5/2014    Zoppetti et al.

FOREIGN PATENT DOCUMENTS

| JP | S62249935 A | 10/1987 |
|---|---|---|
| WO | 2004024126 A1 | 3/2004 |
| WO | 2006095026 A2 | 9/2006 |
| WO | 2008025819 A2 | 3/2008 |

OTHER PUBLICATIONS

International Search Report and Written Opinion for International Application No. PCT/EP2018/053244 (15 Pages) (dated Apr. 17, 2018).

Pose-Vilarnovo et al., "Effect of Hydroxypropylmethyl Cellulose on the Complexation of Diclofenac With Cyclodextrins", Journal of Thermal Analysis and Calorim, 2003, vol. 73, No. 1, pp. 661-670.

*Primary Examiner* — Benjamin J Packard
(74) *Attorney, Agent, or Firm* — Lucas & Mercanti, LLP

(57) ABSTRACT

New soft gelatin capsules highly protected against the degradation of the active ingredient contained therein and highly resistant to hydration are described. The capsular wall is characterized by containing hydroxypropyl beta cyclodextrin in low quantity with respect to the weight of the wall and sub-stoichiometric with respect to that necessary for complexing the drug contained within the capsule. The new capsules are storage-stable, avoid the development of active ingredient by-products and maintain a high weight constancy, i.e. low hygroscopy.

9 Claims, No Drawings

SOFT GELATIN CAPSULES CONTAINING HYDROXYPROPYL BETA CYCLODEXTRIN WITH HIGH STABILITY

CROSS-REFERENCE TO RELATED APPLICATIONS

This application is a 371 of PCT/EP2018/053244, filed Feb. 9, 2018, which claims the benefit of Italian Patent Application No. 102017000015145, filed Feb. 10, 2017.

FIELD OF THE INVENTION

The present invention relates to the field of pharmaceutical compositions in soft gelatin capsules. New soft gelatin capsules with a high storage stability are described.

BACKGROUND OF THE INVENTION

Soft gelatin capsules are a widely used pharmaceutical form with the purpose of formulating active ingredients which need to be formulated in a liquid or semi-liquid state, but which are poorly soluble in water; the use of this pharmaceutical form is ideal in the case of active ingredients at very low unit doses: in this case, the formulation in solution is preferable to the solid one as it allows a more accurate distribution of the active ingredient in the liquid vehicle, with the advantage of a better dosing accuracy. Furthermore, the formulation of the active ingredient in a liquid vehicle also facilitates the dispersion and the absorption of the drug after the capsular wall has been degraded by the body's liquids. Soft gelatin capsules can also be used for water-soluble active ingredients, exploiting in this case other properties, in particular, taste and/or smell masking, easy swallowing, etc.

Soft gelatin capsules have an outer envelope welded in gelatin and an inner liquid or pasty fill, preferably hydrophobic, within which the active ingredient is dissolved or dispersed (e.g., in the form of a suspension, emulsion, microemulsion, etc.). For a review, see e.g. Gullapalli et al., *J. Pharmaceutical Sciences*, 99 (10), 2010, 4107.

All soft gelatin capsules show a certain permeability to oxygen, and a certain propensity to absorb moisture from the environment. The aforesaid phenomena can involve various problems, including an undesired exposure of the active ingredient to environmental factors (air, oxygen, moisture) with possible formation of degradation products. In some instances, this phenomenon has also been visually highlighted, by means of a variation in the colour of the capsular wall caused by degradation products with a non-neutral colour. For example, the Applicant has experimentally found that soft gelatin capsules containing diclofenac or its derivatives over time developed a reddish colour due to oxidation products; the oxidability of diclofenac to red-coloured quinone products is known by Groning et al., *Chemosphere* 69 (2007) 509-516. This phenomenon was found by the Applicant even when the capsules were stored in opaque blisters not allowing the light passage (evidence in the experimental part). This demonstrates the difficulty in preventing the degradation of low stability active ingredients formulated in soft gelatin capsules. Similar degradation phenomena were observed by the Applicant also in the case of soft gelatin capsules containing tadalafil, a well-known drug used in the treatment of erectile problems.

Cyclodextrins are cyclic oligosaccharides consisting of glucopyranose subunits; they are widely used in the pharmaceutical technology, exploiting their ability to form water-soluble complexes with molecules of sparingly water-soluble drugs. Cyclodextrins form a cage-like supramolecular structure, whose cavity can host the active ingredient molecule; the resulting complex, externally hydrophilic due to the numerous hydroxyl functions of the cyclodextrin, allows to bring in an aqueous solution the molecule of the active ingredient which, in the absence of cyclodextrin, would be water-insoluble or slightly soluble (Del Valle et al., *Process Biochemistry*, Volume 39, Issue 9, 31 May 2004, Pages 1033-1046).

The complexation reaction occurs in an aqueous medium, whereby the drug and cyclodextrin molecules are contacted. Therefore, in the instance of solid pharmaceutical forms, the solubilization of the drug into cyclodextrin typically occurs at the time of administration, i.e. when the dosage unit is contacted with the organic liquids or when it is dissolved in a liquid medium, immediately prior to administration.

Occasionally the complexation in cyclodextrin has been carried out to protect the active ingredients from degradation phenomena, however with modest results (*International Journal of Photoenergy*, 3, 2001, 205-211). The same Applicant has found (evidence in the experimental part) that an aqueous solution containing solid diclofenac complexed in hydroxypropyl beta cyclodextrin showed, under storage conditions (25° C.±2° C., 60±5% R.H.) degradation phenomena highlighted by an amber colour: this shows that the complexation mechanism in the hydroxypropyl beta cyclodextrin is not able to effectively protect from degradation phenomena.

U.S. Pat. No. 8,728,519 describes soft gelatin capsules containing a cyclodextrin in the capsular wall; the cyclodextrin is said to form an inclusion complex with the drug present in the fill, the drug being insoluble or poorly soluble in water; capsular compositions containing hydroxypropyl beta cyclodextrin in elevated percentages are described, with embodiments comprised between 14 and 23% on the weight of the capsular wall precursor solution. The document does not address stability problems of the capsular wall and/or fill; the capsules are generically said to have a conventional stability, without specific studies or data in this regard.

Patent application JP-A-62249935 describes hard or soft gelatin capsules; the capsular wall contains less than 10% of cyclodextrins in general (on the weight of the capsular wall precursor solution): the addition of cyclodextrin prevents the hardening of the capsular wall and the lengthening of the disintegration time; the lowest limit of cyclodextrin added to the capsule is not indicated, but the document advises that the effect is not obtainable with a too low cyclodextrin content.

Considering the above, the need is still felt for new active ingredient formulations in soft gelatin capsules that are efficiently protected against degradation phenomena, particularly during storage. There is also a need for capsules that exhibit stability against phenomena such as the degradation of the active ingredient or the instability of the capsular structure. The need for capsules that exhibit a stability against the active ingredient degradation and a high capsular structure stability remains even more felt. There is also a need for soft gelatin capsules that do not show changes in colour or weight variation during storage. The need for soft gelatin capsules that do not present neither colour variation nor weight variation during storage remains even more felt. There is also a need for soft gelatin capsules which are protected by the aforesaid phenomena, wherein said capsules contain therein selected classes of active ingredients particularly liable to degradation phenomena.

These and further problems are addressed and solved by the invention object of the present application.

SUMMARY

It has now unexpectedly been found that the hydroxypropyl beta cyclodextrin, incorporated in the capsular wall of soft gelatin capsules in low and insufficient amount to form an inclusion complex with the active ingredient present in the fill, preferably in association with specific plasticizers present in the capsule within certain weight ratios, obtains a particular and unexpected stabilization of the capsule upon storage: the stabilization occurs as a synergy of two effects, i.e. an improved protection against the degradation of the active ingredient contained in the fill, and a reduced hygroscopy of the capsular wall: such effects have been experimentally found by the Applicant as a reduced colour variation of the capsule (caused by the formation of non-neutral colour degradation products) and a reduced weight increase of the capsule exposed to moisture. Therefore, the invention is directed to a soft gelatin capsule having inside a fill comprising an active ingredient, wherein the wall of said capsule comprises hydroxypropyl beta cyclodextrin (HPBCD) in an amount being: (a) less than 10% by weight on the weight of the wall and (b) sub-stoichiometric to form an inclusion complex with the active ingredient present in the fill.

DETAILED DESCRIPTION OF THE INVENTION

According to the present invention, the term "sub-stoichiometric amount of HPBCD" means that the HPBCD contained in the capsular wall is present in a molar ratio lower than 1:1 with respect to the active ingredient present in the fill (or, in an alternative and equivalent definition, the active ingredient contained in the fill is present in a molar ratio higher than 1:1 with respect to the HPBCD contained in the capsular wall).

In addition to being present in sub-stoichiometric amount, HPBCD is present in a low amount with respect to the weight of the capsular wall. Specifically, it is present in amounts less than 10% (e.g. between 1% and 8%) on the weight of the capsular wall; in the present application, "weight of the capsular wall" means the total weight of all the components of the wall excluding water (which is added separately during the preparation of the capsular wall and subsequently evaporated to obtain the finished product) and excluding the fill inside the capsule. Instead, if compared to the capsular wall "in wet phase" (i.e. to the capsule precursor solution, during the preparation step thereof), the HPBCD is used in amount less than 7% by weight (for example comprised between 0.5% and 6%, or between 0.5% and 2%); capsular wall "in wet phase" means the total weight of the wall components, including the water added during the preparation step thereof, and excluding the fill inside the capsule. The two aforementioned modes of expression of the HPBCD (with respect to the precursor solution or the finished capsule) can be used indifferently and in combination with each other to indicate the amount of HPBCD used in the present invention, in association with all other general characteristics of the capsule.

The active ingredient present in the fill is characterized by containing one or more nitrogen atoms. In fact, it is known that these atoms can react in the presence of oxygen, forming N-oxides, hydroxylamines, conjugated systems or other degradation products. Within this group, a favoured class is the one of the active ingredients containing a phenylamine sub-unit in their structural formula; it is known that such a structure is easily degradable forming quinoneimine products with non-neutral colour: e.g. diclofenac, DHEP (diclofenac epolamine) and pharmaceutically acceptable salts and derivatives thereof belong to this class. Another favoured class is the one of the active ingredients which contain nitrogen heterocycles in their structural formula, in particular pyrrolidine and/or indole: examples of this class are tadalafil and DHEP and pharmaceutically acceptable salts and derivatives thereof.

Accordingly, one embodiment of the present invention is a soft gelatin capsule having inside a fill comprising an active ingredient containing nitrogen, said active ingredient being a molecule containing one or more phenylamine, indole and/or pyrrolidine sub-units, wherein the wall of said capsule comprises hydroxypropyl beta cyclodextrin (HPBCD) in an amount being: (a) less than 10% by weight on the weight of the wall and (b) sub-stoichiometric to form an inclusion complex with the active ingredient present in the fill. The expressions "molecule containing a phenylamine sub-unit, indole sub-unit and/or pyrrolidine sub-unit" means herein a molecule comprising, within its structural formula, a moiety corresponding respectively to phenylamine, indole or pyrrolidine, each of them being optionally fused to other rings and optionally substituted.

In the present capsules, mixtures of two or more active ingredients are also possible, wherein at least one of the present active ingredients contains nitrogen according to one of the definitions presented above. In one version of the invention, the used active ingredient (or mixture thereof, if applicable) does not include vitamins or steroidal compounds. Accordingly, a further embodiment of the present invention is a soft gelatin capsule having inside a fill comprising an active ingredient containing nitrogen, said active ingredient not including vitamins or steroidal compounds, wherein the wall of said capsule comprises hydroxypropyl beta cyclodextrin (HPBCD) in an amount being: (a) less than 10% by weight on the weight of the wall and (b) sub-stoichiometric to form an inclusion complex with the active ingredient present in the fill. The term "vitamins" used herein refers to all vitamins, liposoluble or hydrosoluble; in particular and with no limitation: vitamin A, all vitamins of the B group, vitamin C, vitamin E, vitamin H, vitamin K, etc., and derivatives thereof. The term "steroidal compound" used herein means, as well-known in the art, any compound including in its structural formula the 17-carbon atoms four-fused ring system typical of steroids, e.g. progesterone.

An even further embodiment of the present invention is a soft gelatin capsule having inside a fill comprising an active ingredient containing nitrogen, said active ingredient said active ingredient not including vitamins or steroidal compounds and being a molecule containing one or more phenylamine, indole and/or pyrrolidine sub-units, wherein the wall of said capsule comprises hydroxypropyl beta cyclodextrin (HPBCD) in an amount being: (a) less than 10% by weight on the weight of the wall and (b) sub-stoichiometric to form an inclusion complex with the active ingredient present in the fill.

In a further embodiment, the active ingredient is a water-soluble one, i.e. it has a water solubility at room temperature (20° C.) higher than 0.1% w/v, preferably higher than 0.5% w/v, or more preferably higher than 1% w/v. An example of such active agent is DHEP (having solubility of about 1.9% w/v). This embodiment has the particularity of using HPBCD in connection with an active principle which does not require at all cyclodextrin-mediated solubilization. According to this embodiment, the present invention is characterized as a soft gelatin capsule having inside a fill comprising a water-soluble active ingredient containing nitrogen, wherein the wall of said capsule comprises hydroxypropyl beta cyclodextrin (HPBCD) in an amount being: (a) less than 10% by weight on the weight of the wall and (b) sub-stoichiometric to form an inclusion complex with the active ingredient present in the fill.

Depending on its solubility and the type of vehicle used for the fill, the drug may be present in the fill in the form of solution or dispersion.

In the present formulations, the active ingredient is not complexed or substantially not complexed during the entire production and storage period; the term "substantially" takes into account the normal experimental variability, so that a possible (negligible) complexation at the interface between fill and capsular wall is not excluded a priori. The non-complexation or substantial non-complexation of the active ingredient is due to the concurrence of three factors: (i) the low percentage of HPBCD present in the capsular wall, (ii) the sub-stoichiometry of HPBCD with respect to the active ingredient present in the fill, and (iii) the fact that the active ingredient is not co-formulated with HPBCD but is physically separated from it, i.e. separately formulated in the fill; therefore, during storage, the molecules of HPBCD and of the active ingredient do not substantially come in contact with each other (as would be the situation in a solution of active ingredient and HPBCD or in an intimate physical mixture thereof). The observed stability of the formulation during storage, in particular of the active ingredient contained therein, appears surprisingly not attributable to a complexation mechanism: in particular, it is surprising that a stabilization effect has been obtained by preventing rather than favouring the complexation conditions. The aforementioned presence of HPBCD has also surprisingly increased the resistance of the capsular wall to environmental moisture; this effect is also unexpected, considering that HPBCD is not known for this specific activity and furthermore its percentage amount in the capsular wall is considerably low, therefore prima facie not significantly influencing the properties of the wall itself.

For the purposes of the present invention, the presence of specific plasticizers, i.e. sorbitol and glycerol in a specific weight ratio with each other and, as a whole, with respect to the weight of the capsular portion is important. Specifically, in the soft gelatine capsule according to any of the herein disclosed embodiments of the present invention, glycerol is present in greater amounts than sorbitol, in a weight ratio ranging between 1.1:1 and 1.3:1; moreover, the total amount by weight of glycerol+sorbitol with respect to the weight of the capsular wall (in the dry state) is greater than 25%; preferably it is comprised between 27% and 40%, more preferably between 27% and 35%. Glycerol and sorbitol can be used in the various commercially available forms: e.g. 98% anhydrous glycerol, partially dehydrated sorbitol, etc.

In addition to the aforesaid characteristic ingredients, the capsular wall may comprise further excipients commonly used in the production of soft gelatin capsules. Among them, water (added to the solution from which the capsular wall is obtained), opacifiers, dyes, flavouring agents, etc., can be mentioned.

The fill present in the capsules of the invention can be obtained according to teachings per se known. In particular, it can be lipophilic or hydrophilic based on the liquid vehicle that characterizes it. Non-limiting examples of vehicles for lipophilic fills are: free fatty acids (e.g., oleic acid); fatty acid esters with hydroxyl compounds such as ethyl alcohol, propylene glycol, sucrose, polyethylene glycol, etc.; esters of polyethoxylated fatty acids with short (<C8), medium (C8-C10) or long (>C10) chain, etc. Non-limiting examples of vehicles for hydrophilic fills are polyethylene glycols (e.g., PEG400 or PEG600), methoxy polyethylene glycols (e.g., MPEG350, MPEG550), monoethyl ester of diethylene glycol (Transcutol®), tetrahydrofurfuryl alcohol (Glycofurol), propylene carbonate, N-methyl-2-pyrrolidone (NMP), polyoxyethylene-polyoxypropylene copolymers (Poloxamers), propylene glycol, glycerine, ethyl alcohol, water, etc.

The present capsules are further characterized based on their stability to temperature and humidity. In particular, any of the aforementioned embodiments of the invention can be further characterized in that the soft gelatine capsule shows: a) weight increase lesser than 2%, preferably less than 1%, after storage at 30° C. and 65% relative humidity for 24 months and/or b) no color change after storage at 40° C. and 75% relative humidity for 30 days. These properties ensure an optimal long-term stability when the capsule is packaged in a conventional pharmaceutical blister.

The preparation process of the present capsules comprises, in its general form, the following steps:

(i) preparing a fill comprising an active ingredient;

(ii) preparing a capsular wall precursor solution, comprising gelatin, HPBCD and water;

(iii) integrating products of steps (i) and (ii) to form one or more soft gelatin capsules, the wall thereof containing an amount of HPBCD less than 10% by weight on the weight of the wall and sub-stoichiometric to form an inclusion complex with the active ingredient present in the fill.

The process can be further adapted, in the amounts of the used ingredients, to obtain all the sub-characteristics previously illustrated for the capsules themselves. The capsule formation methods are not determinant and can be varied according to known teachings (see e.g. Gullapalli et al., *J. Pharm. Sci.*, 2010, 99 (10), pp. 41-07-4148); for example, the rotary die process can be mentioned, wherein the capsular wall precursor solution is hot-fed on cooled rotary drums, to form gelatin strips in a semi-liquid state; the strips are taken from the rotating drums and fed on rollers provided with moulds adapted to form a part of the capsule (semi-capsule); in the resulting cavities of the semi-capsule the required amount of fill is injected, and the thus filled semi-capsules are welded together by application of heat and pressure and released from the drum, to form the finished capsule.

EXPERIMENTAL

Example 1: Chromatic Stability Tests on Reference Formulations

Soft gelatin capsules containing diclofenac or its derivatives over time develop a reddish colour due to oxidation products (Gröning et al., *Chemosphere* 69 (2007) 509-516).

This degradation phenomenon has been confirmed by means of colour stability tests carried out on soft gelatine capsules, stored in blisters opaque to light. To this end, soft gelatin capsules were produced having the following composition:

TABLE 1

| Ingredients | Amount (mg/cps) |
|---|---|
| Diclofenac Epolamine (DHEP) | 65.0 |
| Excipients - Fill | |
| Polyethylene glycol 600 | 317.0 |
| Purified water | 25.0 |
| Glycerol, anhydrous (98%) | 18.0 |
| Weight of the fill | 425.0 |
| Excipients of the Capsular Wall | |
| Gelatin | 107.8 |
| Glycerol, anhydrous (98%) | 27.5 |
| Liquid sorbitol, part. dehydrated | 23.0 |
| Sodium hydroxide | 0.6 |
| Purified water | 97.1 |
| Weight of the capsular wall | 256.0 |

The capsules were packaged in opaque blisters and stored for 36 months under one of the following environmental conditions:
(i) room temperature,
(ii) 25° C./60% R.H., or
(iii) 30° C./65% R.H.

To better evaluate the degradation degree, the colour of the fill (primary origin of the chromatic variation of the capsular wall) has been directly examined. Therefore, at the end of the storage period, the capsules were opened, and the liquid fill was separated for visual assessment of the colour degree.

All tested samples (i)-(ii)-(iii) showed a non-neutral colour; moreover, samples (ii) and (iii) showed a progressive increase in colour (browning) compared to sample (i). Experimental confirmation of the degradation of the active ingredient encapsulated during storage was thus verified; furthermore, the packaging in opaque blisters was not able to prevent the variation of colour, which increases according to the level of environmental stress.

Another experiment was carried out by submitting a tadalafil solution (2% by weight in PEG600) under accelerated stress conditions (40° C./75% R.H. for 2 weeks): even in this case, at the end of the test, the solution (but not the control solution free of tadalafil) has developed an evident yellow colour, due to the active ingredient degradation.

Finally, storage stability tests were carried out with various aqueous solutions of diclofenac sodium entirely complexed with hydroxypropyl beta ciclodextrin (HPBCD), having the following composition: diclofenac sodium 40.6 mg; HPBCD 177.6 mg; purified water 782.4 mg. The solutions, after 18 months of storage at 30° C. and 65% R.H., have developed an evident amber colour.

In similar experiments it was verified that the complexation in HPBCD of tadalafil did not prevent the browning of the solution under storage.

These experimental evidences show that the phenomenon of browning is common both to the solution of the non-complexed active ingredient and to the solution of the complexed active ingredient. In particular, the complexation of the active ingredient in HPBCD was not able to prevent the browning of the solution.

Example 2: Formulations According to the Invention

Example 2A capsules according to the present invention, containing DHEP, were made with the following composition:

Formulation of the capsular wall:

| | % w/w | mmg/cps | mmg/cps | mmg/cps |
|---|---|---|---|---|
| Gelatin | 664.71 | 446.60 | 665.41 | 1104.65 |
| Glycerol, anhydrous (98%) | 116.54 | 111.91 | 116.72 | 226.75 |
| Sorbitol, liquid, partially dehydrated | 113.79 | 99.93 | 113.94 | 222.30 |
| HPBCD | 44.59 | 33.31 | 44.64 | 77.42 |
| Sodium hydroxide | 00.37 | 00.26 | 00.37 | 00.59 |
| Weight of the capsular wall | 1100.00 | 772.01 | 1101.08 | 1161.71 |

Formulation of the fill:

| | % w/w | mmg/cps | mmg/cps | mmg/cps |
|---|---|---|---|---|
| Diclofenac Epolamine (DHEP) | 115.29 | 115.38 | 332.5 | 665.0 |
| Polyethylene glycol 600 (Macrogols) | 774.59 | 775.00 | 1158.5 | 3317.0 |
| Purified water | 55.88 | 55.92 | 112.5 | 225.0 |
| Anhydrous glycerol (98%) | 44.24 | 44.26 | 99.0 | 118.0 |
| Weight of the fill | 1100.00 | 1100.56 | 2212.5 | 4425.0 |

Example 2B capsules containing DHEP, without or with HPBCD (according to the present invention) in the capsular wall, have been made, having the following compositions:

| Ingredients | Batch A Amount (mg/cps) | Batch B Amount (mg/cps) | Batch C Amount (mg/cps) |
|---|---|---|---|
| Formulation of the fill | | | |
| Diclofenac Epolamine | 16.25 | 16.25 | 16.25 |
| Polyethylene glycol 600 | 79.25 | 79.25 | 79.25 |
| Purified water | 6.25 | 6.25 | 6.25 |
| Glycerol, anhydrous (98%) | 4.50 | 4.50 | 4.50 |
| Weight of the fill | 106.25 | 106.25 | 106.25 |
| Formulation of the capsular wall | | | |
| Gelatin | 46.60 | 46.60 | 46.60 |
| Glycerol, anhydrous (98%) | 11.91 | 11.91 | 11.91 |
| Sorbitol, liquid, partially dehydrated | 9.93 | 9.93 | 9.93 |
| HPBCD | — | 3.31 | 5.70 |
| Sodium hydroxide | 0.26 | 0.26 | 0.26 |
| Purified water | 45.30 | 41.99 | 39.60 |
| Weight of the capsular wall | 114.0 | 114.0 | 114.0 |

Example 2C

A capsule according to the present invention, containing tadalafil, was made with the following composition:

| | mg/CPS |
|---|---|
| Excipients of the Fill | |
| Polyethylene glycol 600 (PEG 600) | 590.00 |
| Anhydrous glycerine | 33.50 |
| Purified water | 46.60 |
| TADALAFIL | 20.00 |
| Excipients of the shell | |
| Gelatin LB 160 | 114.5200 |
| Sorbitol Special Polyol solution | 24.3600 |

-continued

|  | mg/CPS |
|---|---|
| Anhydrous glycerine | 28.0000 |
| HPB ciclodextrine | 1.9600 |
| Titanium dioxide paste (SC0964 Mastercote White) | 2.8000 |
| Quinoline yellow | 0.1330 |
| Sunset Yellow | 0.0014 |
| Purified water | 108.2256 |

Example 3: Degradation Stability Tests

The capsules prepared in Example 2B (batches A and C) were stored under storage conditions (at room temperature, or at 40° C. and 75% R.H.) for 30 days. At the end of the test, the liquid fill was extracted by cutting the capsules and pouring their content which was chromatically evaluated to determine the presence of coloured degradation products.

After storage at room temperature, the capsules according to the invention (batch C) showed a neutral colour, while the reference ones (batch A) showed a beginning of browning. These differences were much more evident for the capsules stored under stress conditions at 40° C. and 75% R.H., with a much more marked browning for the reference batch, compared to that of the invention.

These evidences demonstrate that the addition of cyclodextrin into the capsular wall, according to the present invention, has significantly reduced the formation of degradation products of the active ingredient present in the fill.

Example 4: Moisture Resistance Tests

The moisture resistance during storage was evaluated for two batches of reference capsules having the composition shown in Example 1, Table 1, with respect to two batches of capsules according to the invention, having the same composition but further containing HPBCD in the capsular wall (7.42 mg of HPBCD per capsule). The capsules were stored at 30° C. and 65% R.H. for a period of 24 months. The weight of the capsules at various times during the test was monitored. The results are shown in the present table.

TABLE 2

| | DHEP 65 mg Without HPBCD | | DHEP 65 mg With HPBCD | |
|---|---|---|---|---|
| Time (Months) | Batch N. 003E08-009 | Batch N. 002E08-009 | Batch N. 013L08-009 | Batch N. 012L08-009 |
| 0 | 604 | 607 | 605 | 608 |
| 3 | 604 | 608 | 605 | 607 |
| 6 | 610 | 612 | 606 | 608 |
| 9 | 616 | 615 | 606 | 610 |
| 12 | 620 | 621 | 609 | 612 |
| 24 | 634 | 634 | 610 | 614 |

These data show that the addition of HPBCD to the capsular wall has reduced very clearly (about 5 times) the rate of weight increase of the capsules exposed to moisture.

The invention claimed is:

1. Soft gelatin capsule having inside a fill comprising an active ingredient containing nitrogen, wherein the wall of said capsule comprises hydroxypropyl beta cyclodextrin (HPBCD) in an amount being: (a) less than 10% by weight on the weight of the wall and (b) sub-stoichiometric to form an inclusion complex with the active ingredient present in the fill, wherein said active ingredient is selected from the group consisting of diclofenac, diclofenac-epolamine (DHEP), tadalafil, or salts thereof.

2. Capsule according to claim 1, wherein the amount (a) of HPBCD is between 1% and 8%.

3. Capsule according to claim 1, wherein the wall comprises sorbitol and glycerol in an overall weight amount being higher than 25% on the weight of said wall and wherein said sorbitol and glycerol are present in a mutual weight ratio between 1.1:1 and 1.3:1.

4. Capsule according to claim 3, wherein said overall weight amount of glycerol and sorbitol is between 27% and 40% or between 27% and 35%.

5. Pharmaceutical composition comprising one or more soft gelatin capsules as described in claim 1.

6. Process for the preparation of one or more soft gelatin capsules as described in claim 1, comprising:
   (i) preparing a fill comprising an active ingredient selected from the group consisting of diclofenac, diclofenac-epolamine (DHEP), tadalafil, or salts thereof;
   (ii) preparing a precursor solution of a capsular wall, comprising gelatin, HPBCD and water;
   (iii) integrating the products of step (i) and (ii) to form one or more soft gelatin capsules, the wall thereof containing an amount of HPBCD less than 10% by weight on the weight of the wall and sub-stoichiometric to form an inclusion complex with the active ingredient present in the fill.

7. Process according to claim 6, wherein the amount of HPBCD in the wall is between 1% and 8% by weight on the weight of the wall.

8. Process according to claim 6, wherein the wall comprises sorbitol and glycerol in an overall weight amount higher than 25% of the weight of the wall and wherein said sorbitol and glycerol are present in a mutual weight ratio comprised between 1.1:1 and 1.3:1.

9. Process according to claim 8, wherein said overall weight amount of glycerol and sorbitol is between 27% and 40% or between 27% and 35%.

* * * * *